(12) United States Patent
Zhang et al.

(10) Patent No.: US 8,505,544 B2
(45) Date of Patent: Aug. 13, 2013

(54) OPTICALLY-IMPLEMENTED MICROSURGERY SYSTEM AND APPROACH

(75) Inventors: Xiaojing Zhang, Austin, TX (US); Olav Solgaard, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 2179 days.

(21) Appl. No.: 11/444,286

(22) Filed: May 31, 2006

(65) Prior Publication Data

US 2011/0160744 A1  Jun. 30, 2011

Related U.S. Application Data

(60) Provisional application No. 60/686,154, filed on May 31, 2005.

(51) Int. Cl.
*A61M 5/20* (2006.01)

(52) U.S. Cl.
USPC ............................................. 128/898; 606/1

(58) Field of Classification Search
USPC ................................. 606/1, 41–49; 128/898
See application file for complete search history.

(56) References Cited

U.S. PATENT DOCUMENTS

| | | | |
|---|---|---|---|
| 4,370,983 A | 2/1983 | Lichtenstein | |
| 4,705,354 A * | 11/1987 | Ulrich | ............................ 356/477 |
| 4,900,303 A | 2/1990 | Lemelson | |
| 4,979,952 A | 12/1990 | Kubota et al. | |
| 5,449,370 A | 9/1995 | Vaitekunas | |
| 5,823,993 A | 10/1998 | Lemelson | |
| 5,993,378 A | 11/1999 | Lemelson | |
| 6,142,939 A | 11/2000 | Eppstein et al. | |
| 6,183,442 B1 * | 2/2001 | Athanasiou et al. | ........... 604/154 |
| 6,391,014 B1 | 5/2002 | Silverman | |
| 6,626,848 B2 | 9/2003 | Neuenfeldt | |
| 6,740,058 B2 | 5/2004 | Lal et al. | |
| 6,767,341 B2 | 7/2004 | Cho | |
| 6,832,988 B2 | 12/2004 | Sproul | |
| 2003/0083619 A1 * | 5/2003 | Angel et al. | ................... 604/141 |
| 2003/0092982 A1 | 5/2003 | Eppstein | |
| 2004/0176717 A1 | 9/2004 | Honda et al. | |
| 2004/0186419 A1 | 9/2004 | Cho | |
| 2004/0200909 A1 | 10/2004 | McMillan et al. | |
| 2004/0220456 A1 | 11/2004 | Eppstein | |
| 2004/0248832 A1 | 12/2004 | Davidson | |
| 2004/0254419 A1 | 12/2004 | Wang et al. | |
| 2005/0027262 A1 | 2/2005 | Appling et al. | |
| 2005/0070959 A1 | 3/2005 | Cichocki | |

* cited by examiner

*Primary Examiner* — Aaron Roane
(74) *Attorney, Agent, or Firm* — Crawford Maunu PLLC

(57) ABSTRACT

According to an example embodiment of the present invention, a vibration-actuated microsurgical system includes an optical force detection arrangement having an optical encoding device configured to modulate an intensity of light in response to a displacement of a portion of the microsurgical system. Light sensing circuitry is configured to detect a force applied to the microsurgical system (e.g., and thereby to a sample) based on the intensity of light sensed from the optical encoding device. This detected force is used in controlling the application of the microsurgical system.

10 Claims, 7 Drawing Sheets

OPTICALLY-IMPLEMENTED MICROSURGERY SYSTEM AND APPROACH

RELATED PATENT DOCUMENTS

This patent document claims the benefit, under 35 U.S.C. §119(e), of U.S. Provisional Patent Application No. 60/686,154, entitled "Optically Calibrated Ultrasonic Microsurgical System" as was filed on May 31, 2005.

FEDERALLY-SPONSORED RESEARCH AND DEVELOPMENT

This invention was made with Government Support under contract MDA972-00-1-0032 awarded by the Defense Advanced Research Projects Agency. The U.S. Government has certain rights in this invention.

FIELD OF THE INVENTION

The present invention relates generally to controlled penetration applications, and more particularly to systems and approaches for injecting or otherwise penetrating a subject such as a biological specimen.

BACKGROUND

Membrane-impermeable macromolecules such as peptides, proteins, oligonucleotides, DNA, RNA, and a variety of other probes can alter or assay cell function. Among available methods for introducing molecules into embryos or cells, such as chemical (ATP, EDTA), vehicular (erythrocyte fusion, vesicle fusion), electrical (electroporation), and mechanical (microinjection, hyposmotic shock, sonication or microprojectiles), microinjection is the standard method for loading embryos and cells. It can reproducibly deliver large numbers of macromolecules to most embryo and cell types with high viability and function. Minimally invasive microinjection and surgical tools with integrated sensors are critical for a wide range of studies in biology and medicine, including calibrated trans-membrane delivery of genetic material into biological model systems, such as *Drosophila* embryos, to enable screening of gene functions.

The knowledge created by genome sequencing has brought unprecedented opportunities to further study the genetic and molecular mechanisms of development and disease. The genome sequence of the fruit fly, (*Drosophila melanogaster*) has enabled systematic studies of the functions of the approximately 13,600 *Drosophila* genes. A powerful technique for learning about gene functions is RNA-interference (RNAi) through microinjections. In RNAi experiments, specific genes are silenced by the presence of dsRNA (double-stranded RNA). An observed change in phenotype indicates the function of the silenced gene. Typically, 100-200 fly embryos per assessed gene are injected during the first 60 minutes of their development, each with 60 picoliters of dsRNA. However, common manual injection involves injecting embryos and cells one at a time with individual glass micropipettes observed under a microscope, which is extremely labor intensive.

Localized and accurate microinjection of genetic material into biological model systems, such as *Drosophila*, is desirable for a variety of studies of developmental biology and genetics. For such studies to be carried out in vivo, the damage caused by the injection must be minimized. Reducing the penetration force is desirable for microinjection systems for biology and genetics studies, such as RNAi for gene silencing. These and other issues continue to present challenges to microsurgical tools and, in particular, to microinjectors for RNAi gene silencing.

SUMMARY

The present invention is directed to overcoming the above-mentioned challenges and others related to applications discussed above and others. These and other aspects of the present invention are exemplified in a number of illustrated implementations and applications, some of which are shown in the figures and characterized in the claims section that follows.

Various example embodiments of the present invention are applicable to penetration-type application such as those directed microsurgical applications such as injection or incision. Some embodiments are directed to microinjectors for sample analysis, such as for RNAi gene silencing.

According to an example embodiment of the present invention, an approach to optical control and/or calibration of vibration-actuated microsurgical-type tools involves illuminating a diffraction phase micrograting coupled to the microsurgical tool and sensing an intensity of light diffracted by the diffraction micrograting. A force applied to the microsurgical tool (and thereby to a sample upon which the tool is acting) is determined based on the intensity of light diffracted by the diffraction micrograting.

According to another example embodiment, a vibration-actuated microsurgical system includes an optical force measuring arrangement having an optical encoding device configured to modulate an intensity of light in response to a displacement of a portion of the microsurgical system. Light sensing and force processing circuitry is configured to detect light from the optical encoding device and to use the intensity of the detected light to detect a force applied to the microsurgical system. In some applications, the detected force is used with a feedback loop for controlling one or both of the actuation and the vibration of the microsurgical tool.

In another example embodiment, a microsurgical system includes a silicon MEMS microsurgical tool with a transducer mechanically coupled to it, the transducer configured to reciprocally displace the tool at a selected frequency. An optical force measuring arrangement including a MEMS optical encoder is coupled to one or both of the microsurgical tool and the transducer. A light source illuminates the optical encoder. Light detection circuitry detects the intensity of light from the optical encoder and uses the intensity to detect a force applied to the microsurgical tool.

According to another example embodiment of the present invention, a sample is surgically treated (e.g., cut, penetrated or otherwise affected) using a vibration-actuated microsurgical tool having a probe tip. The probe tip is vibrationally-actuated and applied to a sample, for example, by laterally or otherwise moving the probe tip against the sample while vibrating the probe tip at a frequency. A diffraction phase micrograting coupled to the microsurgical tool is illuminated, and an intensity of light diffracted by the diffraction phase micrograting is detected. The intensity of light diffracted by the diffraction phase micrograting is used to determine a force applied to the microsurgical tool. The application of the probe tip to the sample is controlled as a function of the determined force.

The above summary is not intended to describe each illustrated embodiment or every implementation of the present invention. The figures and detailed description that follow exemplify various example embodiments.

BRIEF DESCRIPTION OF THE DRAWINGS

The invention may be more completely understood in consideration of the detailed description of various embodiments of the invention in connection with the accompanying drawings, in which.

Figure 1A:
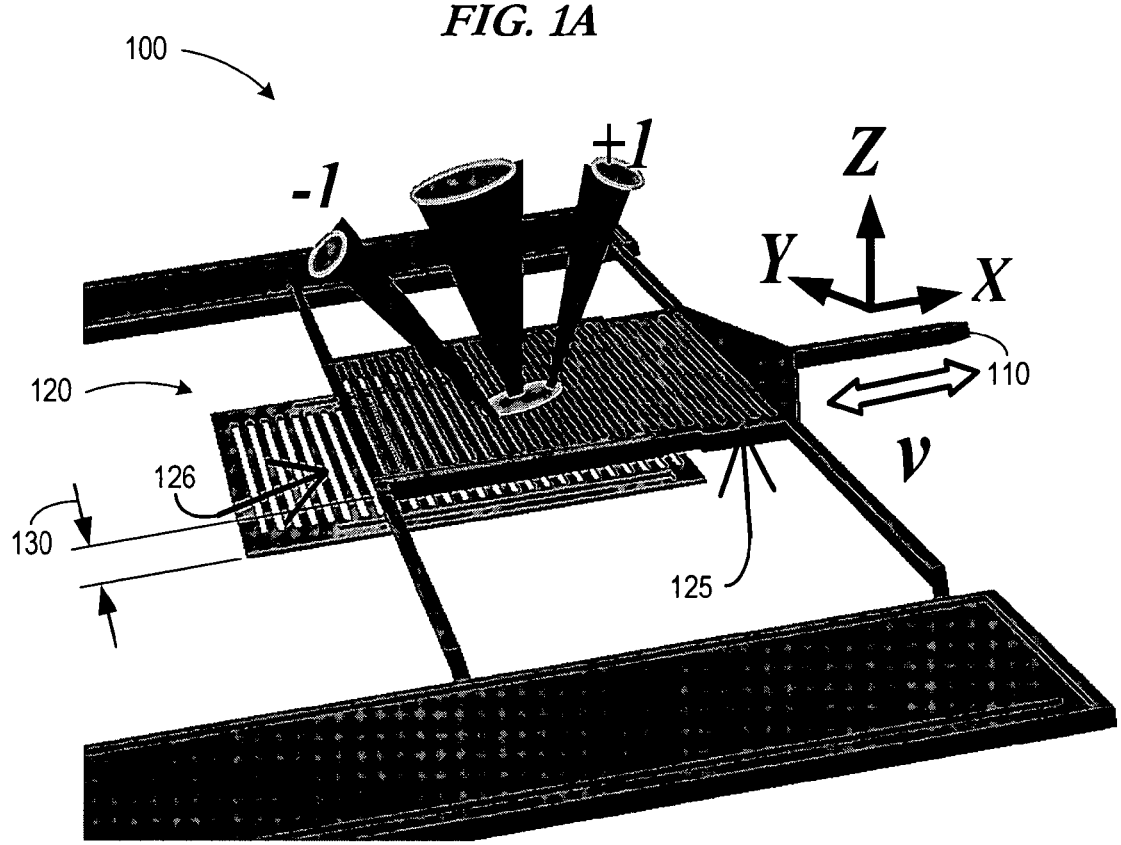
FIG. 1A shows a perspective view of an ultrasonic microinjection system having optical encoding according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the scope of the invention, including that in the appended claims.

DETAILED DESCRIPTION

The present invention is believed to be applicable to a variety of different types of microsurgical-type tools for applications such as injections and other surgical applications, and has been found to be particularly useful for applications involving the optical detection of forces and associated control with vibration-actuated activated microinjectors and microsurgical tools. While the present invention is not necessarily limited to such approaches, various aspects of the invention may be appreciated through a discussion of various examples using these and other contexts.

According to an example embodiment of the present invention, an optical grating arrangement is coupled to a microsurgical tool and responds to pressure applied to the tool (e.g., by deflecting, twisting or otherwise moving). Movement of the optical grating arrangement is optically detected and used to characterize the pressure applied to the tool. In one application, this optical detection approach is used to actively characterize the pressure applied in a microsurgical application, such as to detect that a specimen has been penetrated. In other applications, this optical detection approach is used in a calibration-type environment, where pressure needed for a particular microsurgical application is detected for two or more samples; results are used to calibrate the application of pressure for additional samples.

In some calibration-type applications, the pressure needed for different microsurgical applications is stored in a lookup table having information specified for the different applications. When the microsurgical tool is used for such an application, the lookup table is used to select a force for use in the applications, as relevant to the particular sample or sample type, or a particular type of microsurgical application (e.g., penetration for injection, incision or others).

According to another example embodiment of the present invention, a vibration-actuated microsurgical system, such as a microinjection systems for biology and genetics studies, includes an optical force measuring arrangement having an optical encoding device configured to modulate an intensity of light in response to a displacement of a portion of the microsurgical system. For example, the optical encoding device may include a MEMS (Micro-Electro-Mechanical Systems) diffraction phase micrograting arrangement. Light sensing circuitry is configured to determine a force applied to the microsurgical system based on the intensity of light sensed from the optical encoding device. Optical detection of pressures associated with a vibration-actuated microsurgical tool involves illuminating the diffraction phase micrograting coupled to the microsurgical tool and sensing an intensity of light diffracted by the diffraction micrograting. The force upon the microsurgical tool, and correspondingly to the subject upon which the tool is used, is determined based on the intensity of light diffracted by the diffraction phase micrograting.

In another example embodiment, a calibration-type approach involves the detection of forces applied to a subject with a vibration-actuated microsurgical tool at different vibration frequencies (e.g., extending into the ultrasonic range) and at different rates of translation (movement) of the microsurgical tool against the subject. Using optically-detected information, the pressure applied to the subject is detected and tracked for under different combinations of frequency and translation rates. With this information, a desirable operating frequency and translation rate are selected for a particular application, and used in further microsurgical applications for similar subjects. Such approaches are applicable, for example, to embryos and other subjects that are susceptible to damage during such microsurgical application, or that otherwise benefit from the control (e.g., reduction and/or minimization) of force used in such applications.

In another example embodiment of the present invention, a microinjection system includes a microinjection tool with optical gratings and an optical detector that facilitate detection of the penetration of a subject. The microinjection tool has an injection tip operated in a vibration mode and translated against the subject for penetration, and an elongated tubular structure for delivering (injecting) an agent into the subject after penetration. A signal from the optical detector is used to detect the force applied to the tool (and, correspondingly, to the subject) and to detect that the subject has been penetrated. After penetration, the translation and vibration of the microinjection tool is terminated and the agent is delivered from a proximal end of an elongated tubular structure to a distal end of the elongated tubular structure and into the subject.

In another example embodiment of the present invention a microsurgical system includes an arrangement for illuminating a diffraction phase micrograting coupled to a microsurgical tool. Such an illumination arrangement may include, for example, a laser, an incandescent light, a light emitting diode (LED), an optical conduit such as a fiber optic cable, mirrors and/or other light-based devices. The system also includes a sensing arrangement that senses an intensity of light diffracted by the diffraction phase micrograting. The sensing arrangement may include, for example, an optical sensor such as a photodiode, a phototube or other light-responsive device, as well as light-directing arrangements such as those described with the illumination arrangement above. The system also includes a circuit or other arrangement for determining a force applied to the microsurgical tool based on the intensity of light diffracted by the diffraction phase micrograting. Such a circuit may include, for example, a computer programmed to use information generated from the sensing arrangement (e.g., a value or signal associated with the light sensed) to determine a force as related to a degree of deflection, movement or other condition of the micrograting.

Figure 1B:
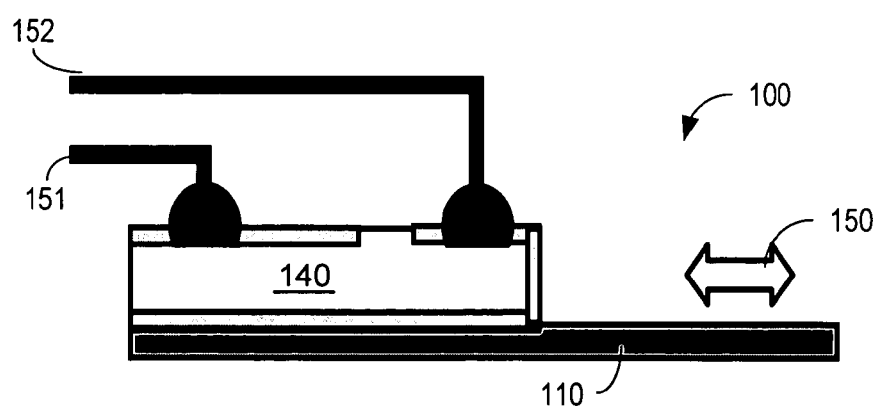
FIG. 1B shows side view of an ultrasonic microinjection system having optical encoding according to another example embodiment of the present invention.

Turning now to the Figures, FIGS. 1A and 1B show a perspective and side view respectively of a vibration-actuated microinjection system 100 having optical encoding, according to another example embodiment of the present invention. In some applications, the microinjection system 100 in FIGS. 1A and 1B includes a silicon-nitride microinjector vibrated by piezoelectric actuators that facilitates microinjection, and in some applications, facilitates ultrasonic vibration or actuation with the microinjection.

A microinjector 110 has an integrated force sensor 120 including a first micrograting 125 and a second micrograting 126. Generally, the microinjector 110 also includes a conduit or other structure for delivering a substance to a specimen. In some applications, an elongated tubular structure is incorporated with the microinjector and extends from a proximal end (e.g., near micrograting 125) to a distal end (e.g., near a tip of the microinjector along the X axis). Injection material such as an agent is delivered from the proximal end of the elongated tubular structure to a distal end of the elongated tubular structure and into the subject.

The microgratings 125, 126 are vertically-separated a separation distance 130, and used as an optical encoder as will be further illustrated below. The two microgratings 125, 126 are aligned when no force or acceleration is applied. The upper first micrograting 125 is connected to the microinjector 110, and has a resonant frequency of, in this example, $f_0 = 14$ KHz.

Referring to FIG. 1B, the microinjection system 100 includes a piezoelectric element 140 that is coupled to a voltage potential via a first electrode assembly 151 and a second electrode assembly 152. In response to a sinusoidally varying electric potential applied across the first electrode assembly 151 and the second electrode assembly 152, the microinjector 110 is reciprocally vibrated. A velocity indicator 150 illustrates longitudinal vibration of the microinjector 110 due to electrical stimulation of the piezoelectric element 140. In some applications, the poling direction of the piezoelectric element 140 and/or the placement of the electrode assemblies 151 and 152 are changed to cause transverse vibration of the microinjector 110 or other desirable vibration modes.

In one example embodiment, a piezoelectric stack, including many piezoelectric ceramic layers that are assembled in series mechanically and in parallel electrically, is bonded onto the back side of the encoder (i.e., microgratings 125 and 126). The piezoelectric stack is used to vibrate the microinjector longitudinally in the X-direction as indicated in FIG. 1A. In some particular embodiments, the piezo-actuator has a resonance frequency of 69 kHz, and a displacement at a (e.g., maximum) drive voltage of 150 volts of 17.4 µm±2.0 µm.

In some applications, a microsurgical-type tool as described herein (e.g., in FIGS. 1A and 1B or otherwise above) is operated in different vibrational modes for different applications. For instance, a microsurgical tool may be programmed or otherwise operated at different select vibrational frequencies and modes to suit the application to a particular sample undergoing analysis. Referring to FIG. 1A by way of example, certain vibrational modes my involve, for example, vibration in the X, Y, or Z direction, rotational vibration about one of the X, Y or Z axis, or vibration in a direction or about an axis that is different than the indicated X, Y or Z axes. In certain applications, these vibrational frequencies are selected to excite selected fundamental modes.

In certain applications, the vibration frequencies and/or modes are selected to facilitate surgical application of a probe tip to a sample while maintaining the flatness of optical gratings for readout. For instance, referring again to FIG. 1A, the microgratings 125 and 126 are desirably maintained in a position amenable to optical detection of light from the microgratings. In this regard, a mode or modes of vibration that facilitate the desirable alignment of the microgratings (e.g., relative to an optical detector) while also facilitating a desirable (e.g., low) pressure to achieve microsurgical treatment (e.g., penetration) of a sample, are selected.

For general information regarding microsurgical applications, and for specific information regarding different modes of vibration and application thereof for microsurgical applications, reference may be made to Zhang, et al., "Microoptical Characterization of Ultrasonic Microinjections on Drosophila Embryos for Genome-wide RNAi Screen", *Journal of Microelectromechanical Systems*, Vol. 15, 2, 2006, which is fully incorporated herein by reference.

Figure 2A:
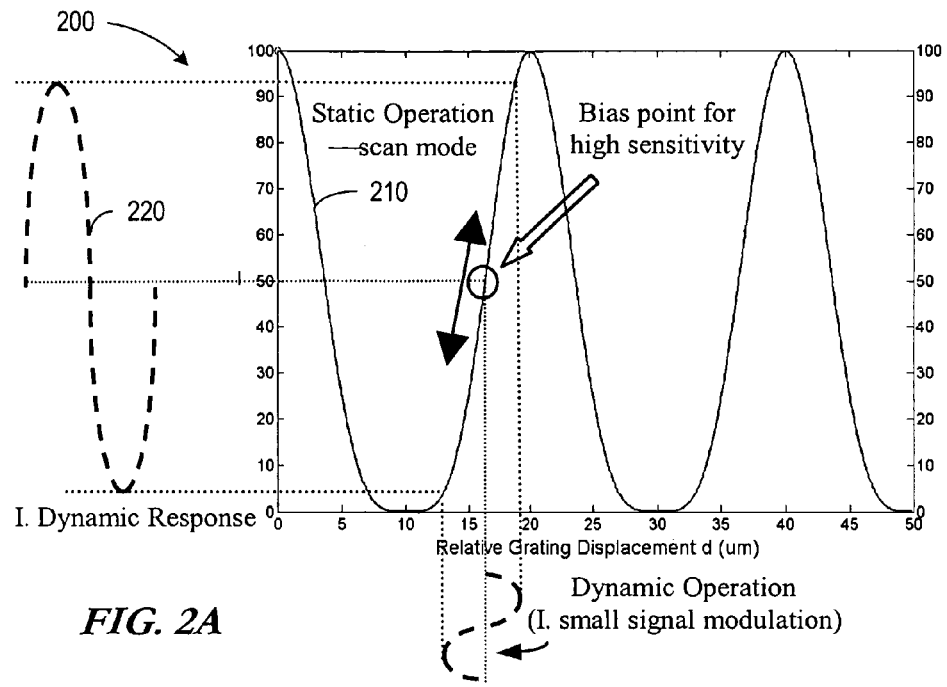
FIG. 2A shows a graph illustrating the dynamic response of optical sensor signals according to an example embodiment of the present invention.
Figure 2B:
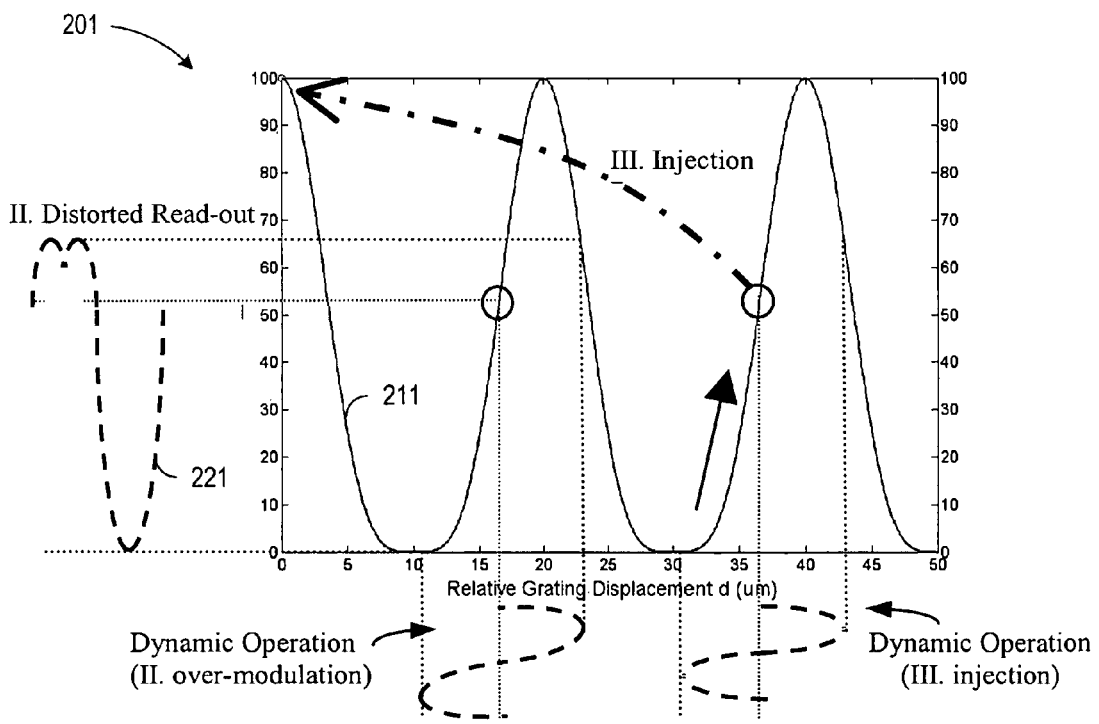
FIG. 2B shows a graph illustrating the dynamic response of optical sensor signals for over-modulation and injection according to an example embodiment of the present invention.

FIGS. 2A and 2B show graphs 200, 201 respectively illustrating the dynamic response of optical sensor signals, according to another example embodiment of the present invention. The static diffraction characteristics of an optical encoder, such as the microgratings 125, 126 illustrated in FIGS. 1A and 1B, can be analyzed by Fraunhofer diffraction theory under normal plane-wave illumination. For purposes of exemplary illustration, the following describes the aforesaid optical sensor signal response in connection with FIGS. 1A and 1B; however, these approaches are applicable for implementation in connection with a multitude of sensor arrangements.

Under vibrational actuation, the index micrograting 126 vibrates along with the microinjector 110, and hence changes its position relative to the fixed scale micrograting 125. The force on the microinjector 110 is determined by the relative displacement, d(t), of the two microgratings 125 and 126, which is determined by the intensity distribution of the diffraction orders. The first diffraction mode intensity, $I_1$, is a periodic function of microinjector 110 displacement, d(t), as shown by a solid curve 210 in FIG. 2A and a solid curve 211 in FIG. 2B. For the first diffraction mode, we have:

$$I_1[d(t)] = \quad (1)$$

$$I_0 \cdot N^2 \cdot \left[\frac{\text{sinc}^2 \frac{N \cdot d(t)}{2L}}{\text{sinc}^2 \frac{d(t)}{2L}}\right] \cdot \left\{[L-d(t)] \cdot \text{sinc}\frac{[L-d(t)]}{4L}\right\}^2 \cdot \sin^2\phi_0 \cdot G[d(t)],$$

where $I_0$ is the illuminating light intensity, N is the number of micrograting periods under illumination, $\phi_0(x)=(2\pi/\lambda)\cdot(n_1-n_0)\cdot t$ is the phase-delay over the thickness of one micrograting finger, 2L is the period of the micrograting, $G[d(t)]=\sin^2\{\pi[L+|d(t)-L|]/4L\}$ is phase-modulating term, $d_0(t)$ is the quasi-static relative displacement of the two microgratings 125 and 126 caused by the linear motion of the microinjector 110 relative to the target, and $d_V(t)$ is the sinusoidal displacement of the microinjector 110 under piezoelectric actuation. The relative displacement can be expressed:

$$d(t)=d_0(t)+d_V(t) \quad (2)$$

where $$d_V(t)=A\cdot\sin(\omega_P\cdot t+\phi_P)=\alpha\cdot V_a\cdot\sin(2\pi\cdot f_P\cdot t+\phi_P) \quad (3)$$

and $\alpha=0.116$ μm/V, $V_a$, $f_p$ are the piezoelectric constant, the actuation voltage, the driving frequency of the piezo-actuator, respectively. The force is related to the displacement through the spring constant, $k_x$, of the encoder:

$$F=k_x\cdot d(t). \quad (4)$$

The penetration of the cell membrane can be caused by either linear or vibration motion of the microinjector. In experimental studies, the linear translation velocity of the microinjector is much smaller than that of the vibration. The average (or peak) penetration force can be derived from the average (or peak) relative displacement of the two microgratings 125 and 126 using, in one particular example, the spring constant of encoder $k_x$=1.85 N/m.

A dotted line 220 in FIG. 2A and a dotted line 221 in FIG. 2B show the evolution of the force sensor output from a sinusoidal signal at small microinjector displacement (case I in FIG. 2A) to a distorted signal (case II in FIG. 2B) as the microinjector vibration amplitude A increases. Penetration, caused by either increased vibration or translation, significantly reduces the force on the microinjector. Consequently, the average relative micrograting displacement goes to zero, and the output signal abruptly changes to a periodic signal with doubled frequency (case III in FIG. 2B).

Figure 3A:
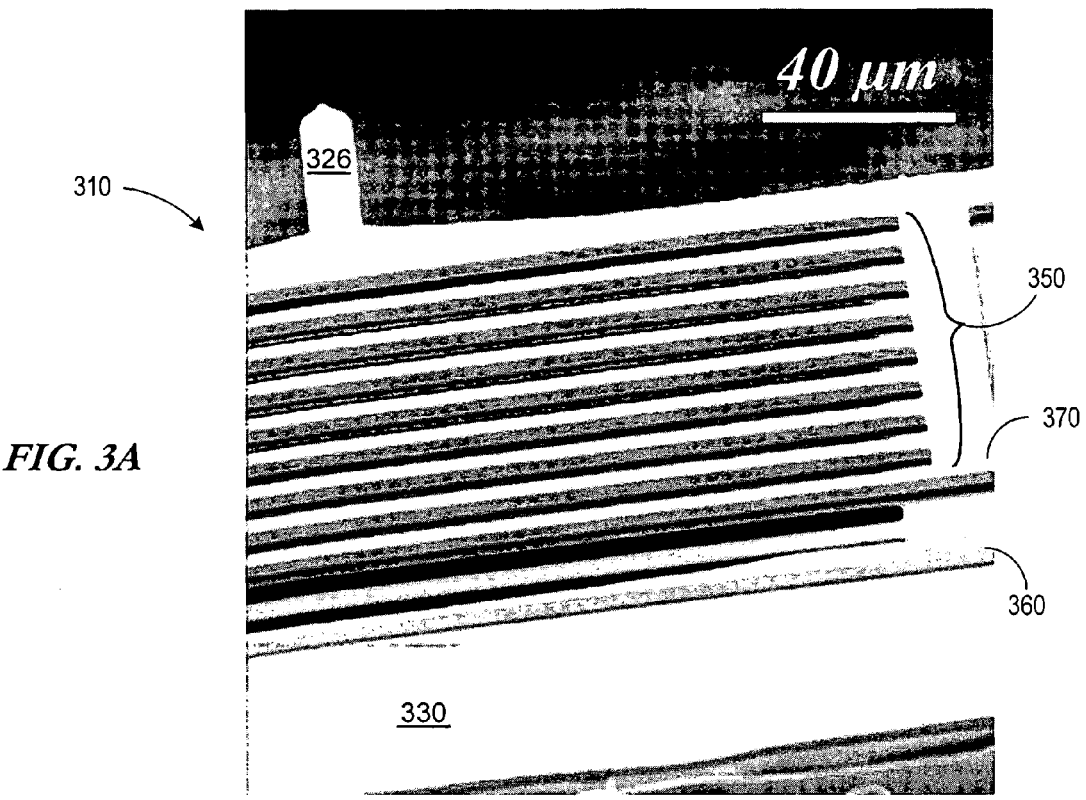
FIG. 3A shows a SEM (Scanning Electron Micrograph) illustrating a top-perspective view of a micrograting useful as an optical encoder according to an example embodiment of the present invention.
Figure 3B:
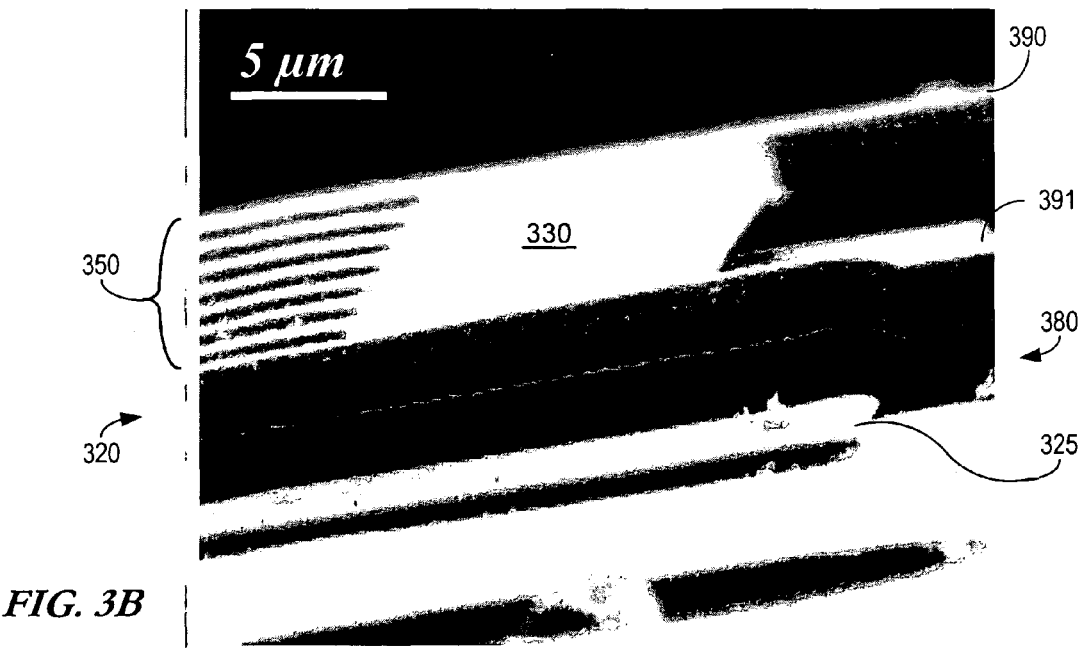
FIG. 3B shows a SEM illustrating a side-perspective view of a micro grating useful as an optical encoder according to an example embodiment of the present invention.

FIGS. 3A and 3B show SEM images illustrating a top-perspective view 310 and side-perspective view 320 respectively of micrograting 350 for an optical encoder 330, according to another example embodiment of the present invention. The optical encoder 330 is fabricated using one or more of a variety of approaches. In one example, two silicon nitride layers for the dual microgratings, separated by low temperature sacrificial oxide, are deposited on the silicon substrates using a chemical vapor deposition (CVD) approach such as LPCVD (Low Pressure Chemical Vapor Deposition) followed by patterning. The SEMs of the micromachined optical encoder force sensor show relatively large vertical gaps suitable for vibrational actuation, such as for ultrasonic actuation.

The SEMs further show a force probe 326 integrated with a movable index micrograting 370 (FIG. 3A) with a side view of the scale grating 360 identified by 325 (FIG. 3B). The scale and index microgratings 360 and 370 are shown with 20 μm pitch, and with a close-view of a 3 μm vertical gap 380 and junction between the microgratings and supporting beams 390, 391 (FIG. 3B).

Figure 4A:
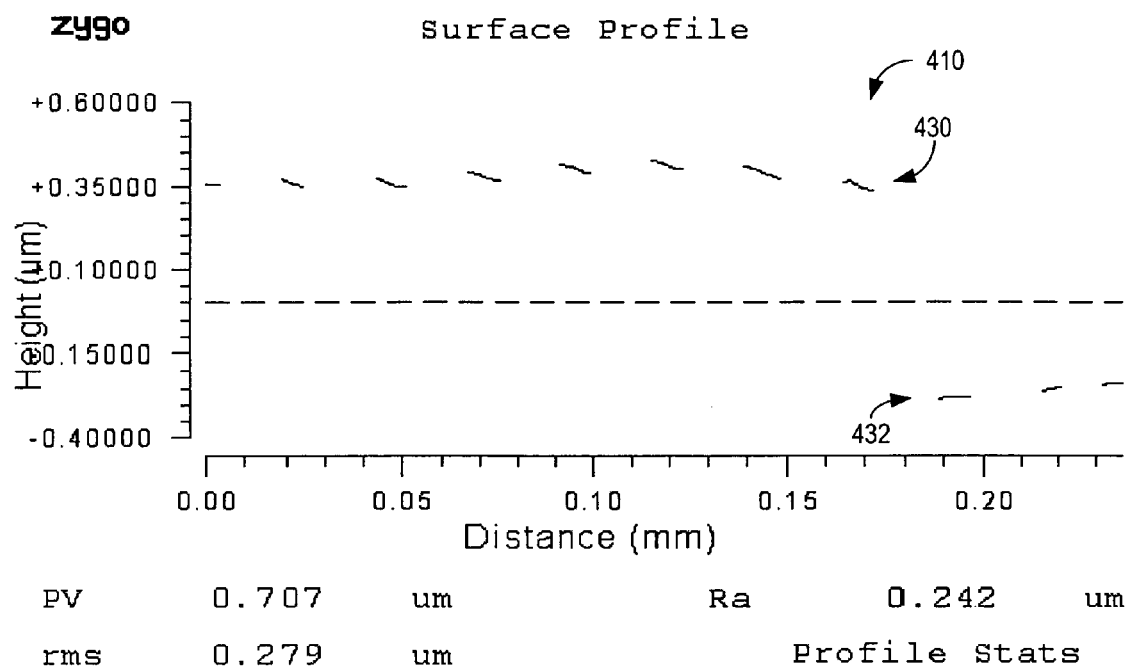
FIG. 4A shows a 2-D graph of a micrograting profile according to an example embodiment of the present invention.
Figure 4B:
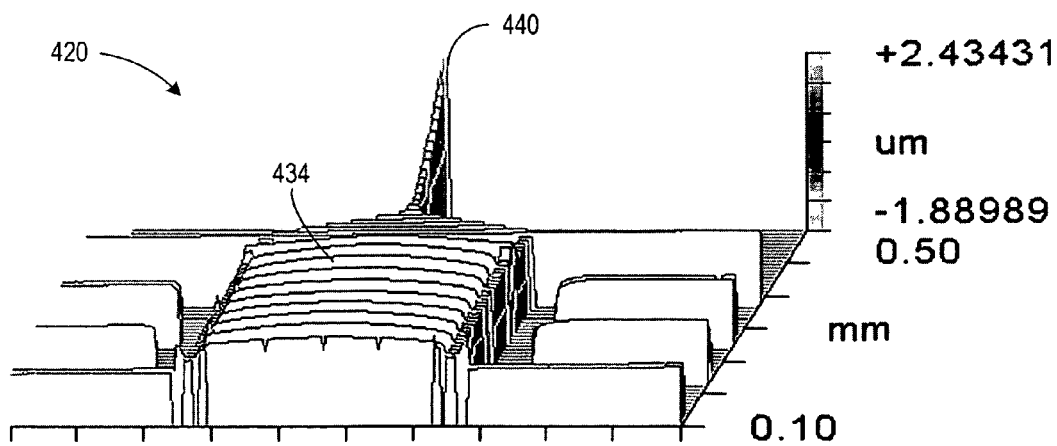
FIG. 4B shows a 3-D graph of a micrograting profile according to an example embodiment of the present invention.

FIGS. 4A and 4B show the surface topography characterization of encoder microgratings with silicon nitride micrograting layers deposited under $NH_3$-rich condition, in connection with another example embodiment of the present invention. Specifically, FIG. 4A shows a 2-D graph 410 of a micrograting profile 412 and FIG. 4B shows a 3-D graph 420 of the micrograting profile 410. Micrograting surfaces 430, 432, 434 have a root-mean-square roughness of less than about 50 nm. Note that overhanging probe 440 (a microinjector, for example) appears to be bending upwards. This is an artifact caused by the shift of optical reference plane due to the removal of the silicon substrate under the probe.

Figure 5:
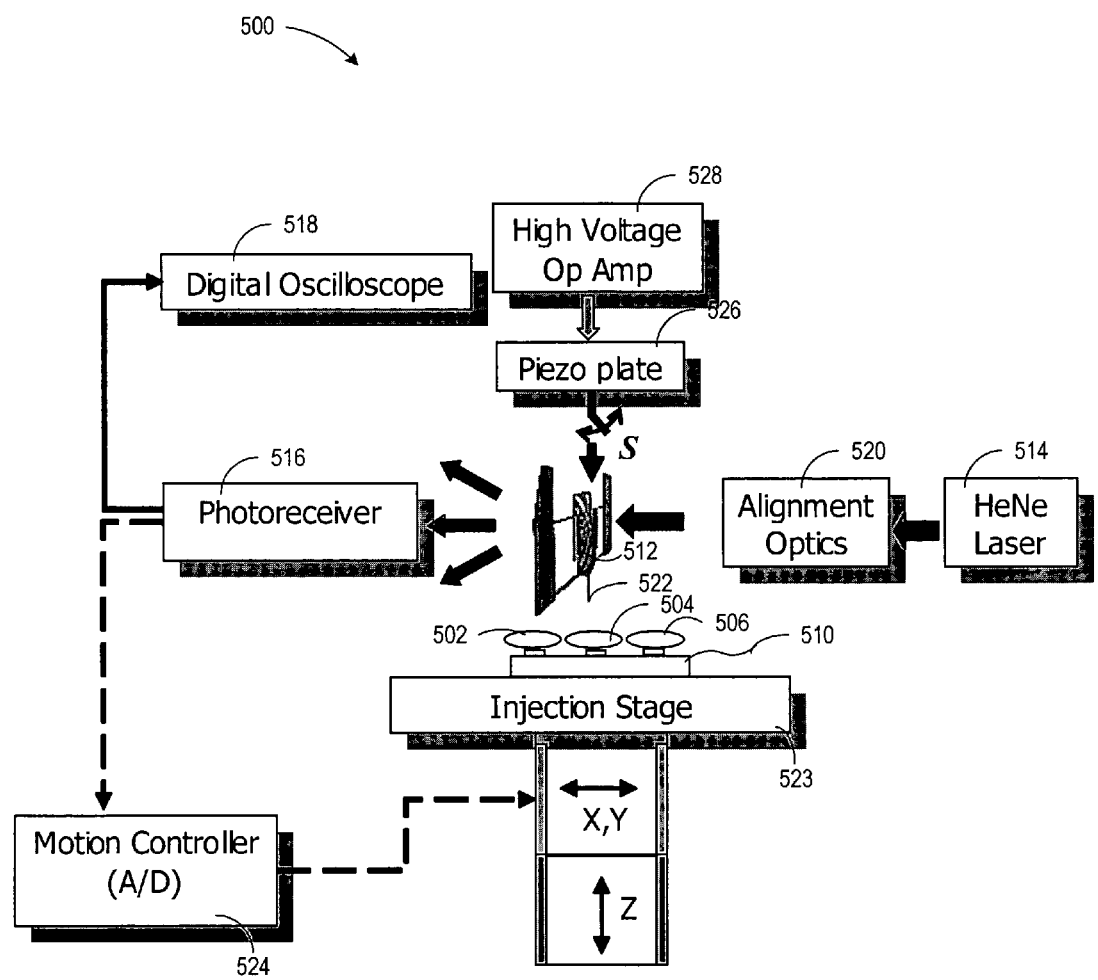
FIG. 5 shows a block diagram of an experimental set-up of an optically encoded force measurement system for an ultrasonically activated microsurgical system according to an example embodiment of the present invention.

FIG. 5 shows a block diagram 500 of an optically encoded force measurement system 500 for an ultrasonically activated microsurgical system, according to an example embodiment of the present invention. The system 500 is applicable to a variety of microsurgical approaches. The following discussion exemplifies one such approach involving in-vivo penetration force characterization experiments; the system 500 is applicable to a variety of such approaches.

Newly hatched *Drosophila* cells 502, 504, 506 are positioned on 2-D micro-fluidic self-assembly chip 510 ready for vertical injection. An optical encoder 512 is illuminated by a HeNe laser 514 (633 nm/4 mW) with spot sizes ranging from 60 to 160 μm to achieve tunable sensitivity, and the output intensity signals are detected using a photoreceiver 516 connected to an oscilloscope 518.

Alignment optics 520 are used to control the light from the laser 514. In some applications, the alignment optics 520 include spatial filtering to minimize cross-talk between diffraction orders and improve the contrast. Static penetration measurements with switch S open (i.e., no ultrasonic actuation) determined an average penetration force of 52.5±13.2% μN and a cell deformation of 58±5.2% μm.

Ultrasonic vibration of the microinjector 522 is controlled by a switch, designated S, which switches a piezo plate 526 driven by a high voltage op-amp 528. During ultrasonic microinjection experiments (S closed), a microinjector 522 was translated towards the target while vibrating. Translation was accomplished by an injection stage 523 controlled by a motion controller 524.

The index-grating vibrates along with the microinjector and hence changes its position relative to the fixed scale micrograting (e.g., as illustrated in FIGS. 1A and 1B). The force acting on the microinjector 522 was determined by the relative displacement of the two microgratings, which was determined by the intensity distribution of the first diffraction order under observation.

The spring constant, k, of optical encoder 512 (W=8 μm, L=10 μm) was measured using the calibration setup illustrated in FIG. 5. The measured value was 1.85 N/m (±8.65%), in reasonable agreement with simulation results (k=2.2 N/m) as derived from encoder displacement vs. force relationship as calculated numerically. Two sets of ultrasonic microinjection experiments were performed to determine microinjector 522 forces and displacements. First the microinjector 522 was brought into contact with the cell to give a fixed bias offset of the two microgratings, i.e., a fixed average force acting on the microinjector. At each bias point, the actuation voltage, and therefore the microinjector tip velocity, was increased until penetration ($f_p$=14 kHz). The peak-to-peak actuation voltage, $V_a$, for penetration is used to calculate the probe vibration amplitude, $d_y=\alpha\cdot V_a$, and tip velocity, $v_p=4\cdot d_y\cdot f_p$.

Figure 6:
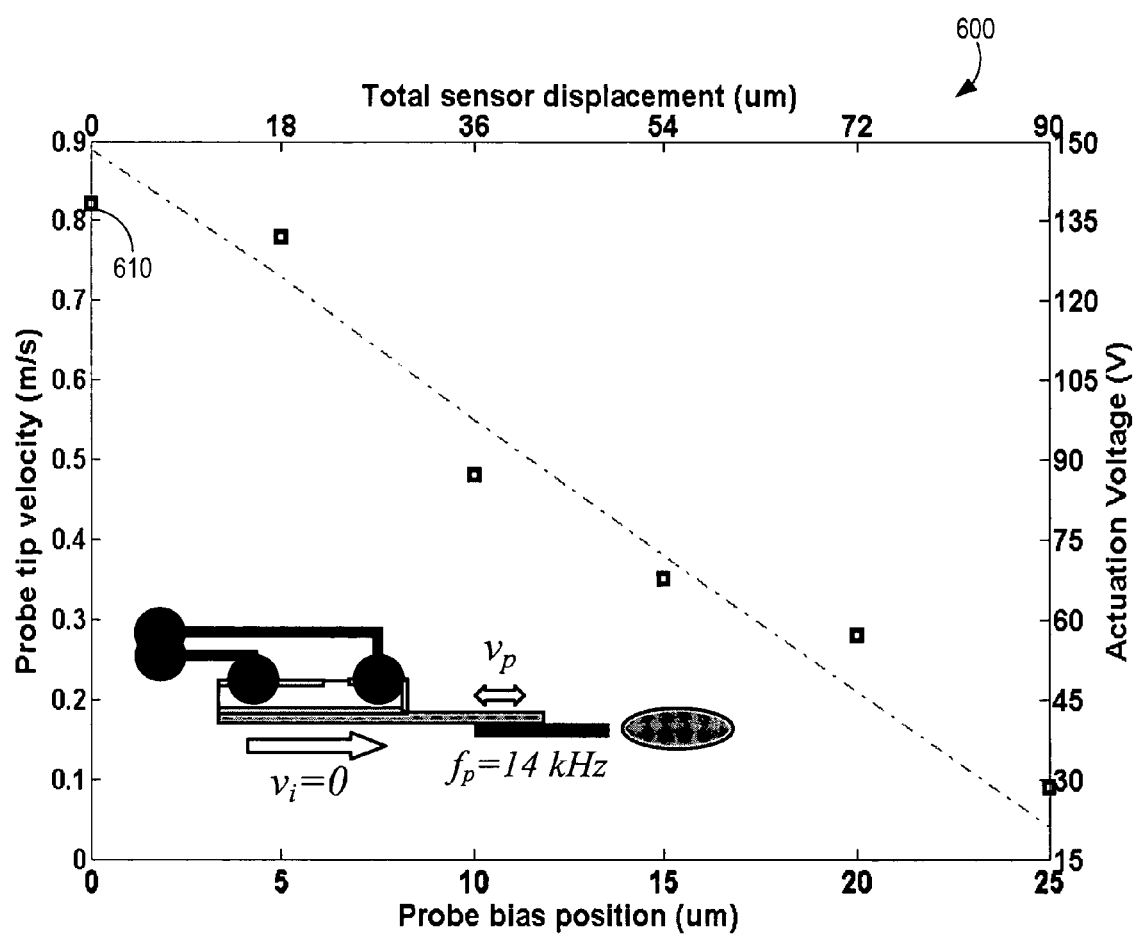
FIG. 6 shows a graph illustrating experimental results for probe tip velocity versus sensor displacement according to an example embodiment of the present invention.

FIG. 6 shows a graph 600 illustrating probe tip velocity versus sensor displacement for a microinjector application, according to another example embodiment of the present invention. As shown in FIG. 6, at a point 610, with zero static force bias, the minimum tip velocity needed for penetration is determined to be about $v_p=0.82$ m/s (actuated at $f_p=14$ kHz and $V_a=126$ V). This corresponds to a peak penetration force of 27.1 µN, or a 48.5% reduction compared to the static penetration without vibration.

Table 1 summarizes calculated tip velocity and the associated peak penetration force at each fixed bias offset of the microinjector, with peak penetration force, $F_p$, versus bias position $d_0$, actuation voltage, $V_a$, vibration amplitude, $d_y$, and tip velocity, $v_p$ shown. In many applications, a linear decrease in the penetration force of about 2.5 µN with every 0.1 m/s tip velocity increase is facilitated.

TABLE 1

Tip velocities and penetration forces.

| $d_0$ (µm) | $V_a$ (V) | $d_v$ (µm) | $v_p$ (m/s) | $F_p$ (µN) |
|---|---|---|---|---|
| 0 | 126 | 14.64 | 0.82 | 27.08 |
| 5 | 120 | 13.93 | 0.78 | 35.02 |
| 10 | 74 | 8.57 | 0.48 | 34.35 |
| 15 | 54 | 6.25 | 0.35 | 39.31 |
| 20 | 43 | 5.00 | 0.28 | 46.25 |
| 25 | 14 | 1.61 | 0.09 | 49.23 |

Figure 7:
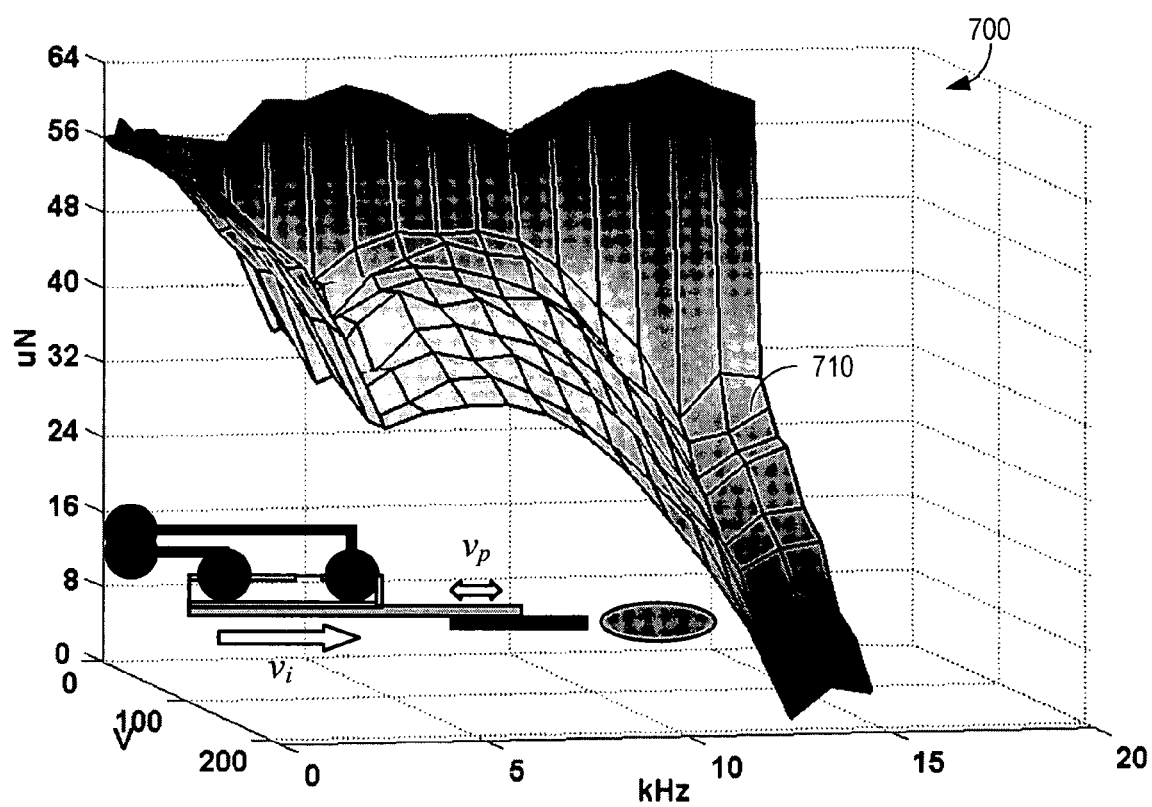
FIG. 7 shows a 3-D graph illustrating experimental results for microinjector force versus voltage and frequency of the ultrasonic microinjector system according to an example embodiment of the present invention.

FIG. 7 shows a 3-D graph 700 illustrating microinjector force versus voltage and frequency for an ultrasonic microinjector system, according to another example embodiment of the present invention. In generating the data presented in graph 700, the vibration amplitude was kept constant and the microinjector was pushed into a cell until penetration. The measured peak penetration force is shown as a function of actuation voltage and frequency, with the points on surface 710 representing an averaged peak penetration force measured across nearby cells (e.g., across 3 to 5 cells). The readout of the total linear injection-stage displacement upon penetration is scaled with respect to the encoder pitch period to get the linear displacement, $d_0$, between the two microgratings, while the amplitude of microinjector vibration is calculated based on the actuation frequency and voltage. The peak force can then be derived from the total relative displacement of the two microgratings.

Both the average and the peak penetration force decrease as the driving frequency and/or actuation voltage increases. At a fixed actuation voltage, the penetration force reached a low value (e.g., a relative minimum) at the encoder resonant frequency of 14 kHz. At the large-value (e.g., relative maximum) actuation voltage of 150 V, the minimum tip velocity for penetration was 0.96 m/s. The minimum peak penetration force was 15.6 µN, about 29.7% of the static penetration force, while the minimum average penetration force was 2.7 µN, about 5.1% of the static penetration force. Using this approach, values for microinjection and/or microsurgical approaches are selectively determined for a variety of applications, with a variety of tools, and in many applications are used to facilitate a relatively low force with high throughput for analyzing specimen.

While certain aspects of the present invention have been described with reference to several particular example embodiments, those skilled in the art will recognize that many changes may be made thereto without departing from the scope of the present invention, aspects of which are set forth in the following claims.

What is claimed is:

1. A method comprising:
illuminating a diffraction phase micrograting coupled to a vibration-actuated microsurgical tool and configured to change position, relative to a fixed scale micrograting and in response to movement of the vibration-actuated microsurgical tool;
sensing an intensity of light diffracted by the diffraction phase micrograting and the fixed scale micrograting; and
determining a force applied to the microsurgical tool based on the sensed intensity of light diffracted by the diffraction phase micrograting.

2. The method of claim 1, further including delivering an agent from a proximal end of the microsurgical tool to a distal end of the microsurgical tool.

3. The method of claim 1, further including reciprocally displacing the microsurgical tool substantially longitudinally.

4. The method of claim 1, further including reciprocally displacing the microsurgical tool substantially transversely.

5. The method of claim 1, wherein determining the force applied to the microsurgical tool comprises determining the force applied to the microsurgical tool in a range of about zero micronewtons to about 70 micronewtons.

6. A method for surgically treating a sample, the method comprising:
vibrationally-actuating and applying a probe tip to a sample;
illuminating a diffraction phase micrograting coupled to a vibration-actuated microsurgical tool and configured to change position, relative to a fixed scale micrograting and in response to movement of the vibration-actuated microsurgical tool;
sensing an intensity of light diffracted by the diffraction phase micrograting and the fixed scale micrograting;
determining a force applied to the microsurgical tool based on the sensed intensity of light diffracted by the diffraction phase micrograting; and
controlling the application of the probe tip to the sample as a function of the determined force.

7. The method of claim 6, wherein controlling the application of the probe tip to the sample as a function of the determined force includes
using the determined force to detect penetration of the sample, and
after detecting penetration, terminating the application of the probe tip to the sample.

8. The method of claim 7, further including, after detecting penetration, injecting a substance into the sample via the probe tip.

9. The method of claim 6, further including
generating a feedback signal characterizing the determined force applied to the microsurgical tool; and
controlling the application of the probe tip to the sample as a function of the feedback signal.

10. The method of claim 6,
wherein vibrationally-actuating and applying a probe tip to the sample includes vibrationally-actuating and applying the probe tip to a plurality of similar samples at different combinations of vibration frequency and rate of application of the probe tip,
wherein determining a force applied to the microsurgical tool based on the intensity of light diffracted by the diffraction phase micrograting includes, for each sample, determining a force applied to the microsurgical tool to effect penetration of the sample,
further including selecting a combination of vibration frequency and rate of application of the probe tip as a function of the determined forces applied to the samples, and further including calibrating the microsurgical tool to use the selected combination of vibration frequency and rate of application of the probe tip for use with analyzing additional similar samples.

\* \* \* \* \*